(12) United States Patent
Yaginuma

(10) Patent No.: US 11,106,880 B2
(45) Date of Patent: Aug. 31, 2021

(54) MANAGEMENT DEVICE AND MANAGEMENT SYSTEM

(71) Applicant: TOSHIBA TEC KABUSHIKI KAISHA, Tokyo (JP)

(72) Inventor: Jun Yaginuma, Izunokuni Shizuoka (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 5 days.

(21) Appl. No.: 16/526,290

(22) Filed: Jul. 30, 2019

(65) Prior Publication Data
US 2020/0065532 A1 Feb. 27, 2020

(30) Foreign Application Priority Data
Aug. 22, 2018 (JP) .............................. JP2018-155476

(51) Int. Cl.
G06K 7/10 (2006.01)
(52) U.S. Cl.
CPC ..... *G06K 7/10366* (2013.01); *G06K 7/10316* (2013.01)
(58) Field of Classification Search
CPC ........... G06K 7/10316; G06K 7/10366; G06K 7/10415; G06K 7/10425; G06K 7/10435; G06K 7/10445; G01N 35/02; G01N 35/10
See application file for complete search history.

(56) References Cited

U.S. PATENT DOCUMENTS

| | | | | |
|---|---|---|---|---|
| 7,903,022 B2 * | 3/2011 | Ohara | ..................... | G01S 13/84 342/127 |
| 9,848,252 B2 * | 12/2017 | Eggers | ..................... | H04Q 9/00 |
| 9,898,630 B2 * | 2/2018 | Nogami | ............... | G06K 7/0008 |
| 10,295,661 B2 | 5/2019 | Kamiya | | |
| 2006/0077039 A1 | 4/2006 | Ibi et al. | | |
| 2009/0303005 A1 * | 12/2009 | Tuttle | ................. | G06K 7/10316 340/10.1 |
| 2009/0303006 A1 * | 12/2009 | Eggers | ..................... | H04Q 9/00 340/10.1 |

FOREIGN PATENT DOCUMENTS

JP  2005-125144 A  5/2005

OTHER PUBLICATIONS

U.S. Appl. No. 16/445,251, filed Jun. 19, 2019 (First Inventor: Jun Yaginuma).

* cited by examiner

*Primary Examiner* — Thien M Le
*Assistant Examiner* — April A Taylor
(74) *Attorney, Agent, or Firm* — Kim & Stewart LLP

(57) ABSTRACT

A management device includes an antenna, a reader, and a processor. The antenna is positionable at a position near a conveyance path. The reader is configured to output wireless tag information based on a radio wave generated by a wireless tag and received by the antenna. The processor is configured to detect passage of an article through a predetermined position on the conveyance path based on an identifier of the article included in the wireless tag information and sign change of a slope of the phase of the radio wave, determine a position of the article based on a timing of the sign change, and store the determined position of the article in correspondence with the identifier of the article.

14 Claims, 6 Drawing Sheets

RELATIONSHIP OF DISTANCE
BETWEEN WIRELESS TAG AND ANTENNA AND PHASE

MANAGEMENT DEVICE AND MANAGEMENT SYSTEM

CROSS-REFERENCE TO RELATED APPLICATION

This application is based upon and claims the benefit of priority from Japanese Patent Application No. 2018-155476, filed on Aug. 22, 2018, the entire contents of which are incorporated herein by reference.

FIELD

Embodiments described herein relate generally to a management device and a management system.

BACKGROUND

In the related art, a barcode or the like is attached to a sample tube, such as a blood collection tube containing a specimen of blood collected from a patient or the like. Identification information for each patient is recorded in or associated with this barcode. Then, the bar code and the identification information are used to associate the patient with the specimen and for managing the sample tube. However, in this case, in order for a reader to read barcodes efficiently, it is necessary to align the orientations of each blood collection tube accommodated in a rack or the like, which takes time and effort.

As a technique for solving this problem, a wireless tag, such as a radio frequency identifier (RFID) tag, attached to a blood collection tube is known. Identification information and the like for each patient is recorded in a wireless tag. Data may be read from and written to the wireless tag through wireless communication regardless of the particular orientation of the wireless tags on the tubes. Therefore, by using wireless tags, it is not necessary to adjust the orientations of the blood collection tubes as would be the case with using barcodes.

However, when using wireless tags as described, if a plurality of blood collection tubes are arranged side by side in a rack, the separation distance between the blood collection tubes is narrow, for example only centimeters or less. For this reason, it will be difficult to determine the position of the specific blood collection tube in the rack on which a any particular wireless tag has been attached. In order to solve such a problem, a technique of providing partitions that blocks radio waves between the blood collection tubes adjacent to each other in the rack has been proposed. However, it is still difficult to sufficiently prevent the influence of radio waves at narrow intervals of centimeters or less utilizing such a partition alone.

DETAILED DESCRIPTION

Figure 1:
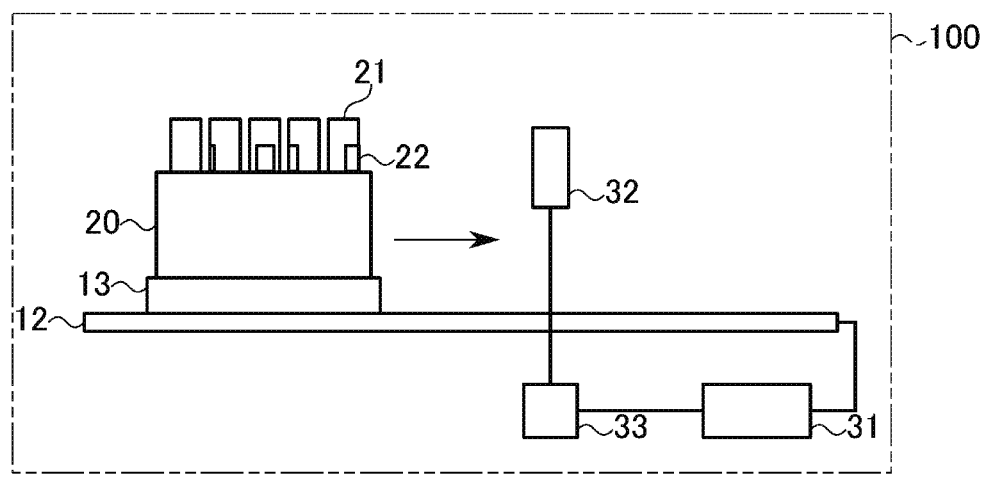
FIG. 1 illustrates a side view of a specifying unit of a specimen inspection system according to a first embodiment and a second embodiment.

In general, according to an embodiment, a management device includes an antenna, a reader, and a processor. The antenna is positionable at a position near a conveyance path. The reader is configured to output wireless tag information based on a radio wave received by the antenna. The processor is configured to detect passage of an article through a predetermined position on the conveyance path based on an identifier of the article included in the wireless tag information and sign change in a slope of a phase of the radio wave received by the antenna, determine a position of the article based on a timing of the sign change, and store the position of the article in correspondence with the identifier of the article. The article including a wireless tag that outputs the radio wave.

Hereinafter, a specimen inspection system according to example embodiments will be described with reference to the drawings. Sizes of elements in the drawings may be exaggerated or modified for convenience of explanation. Moreover, the drawings may omit some certain aspects of for convenience of explanation. The same reference numerals are used for same elements in the drawings.

First Embodiment

Figure 2:
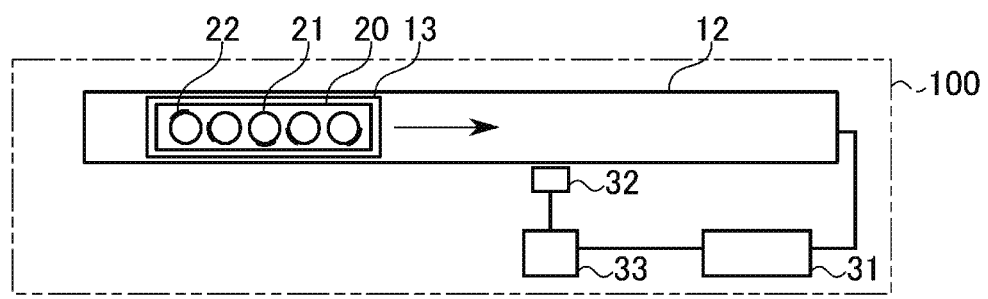
FIG. 2 illustrates a top view of the specifying unit of the specimen inspection system.
Figure 3:
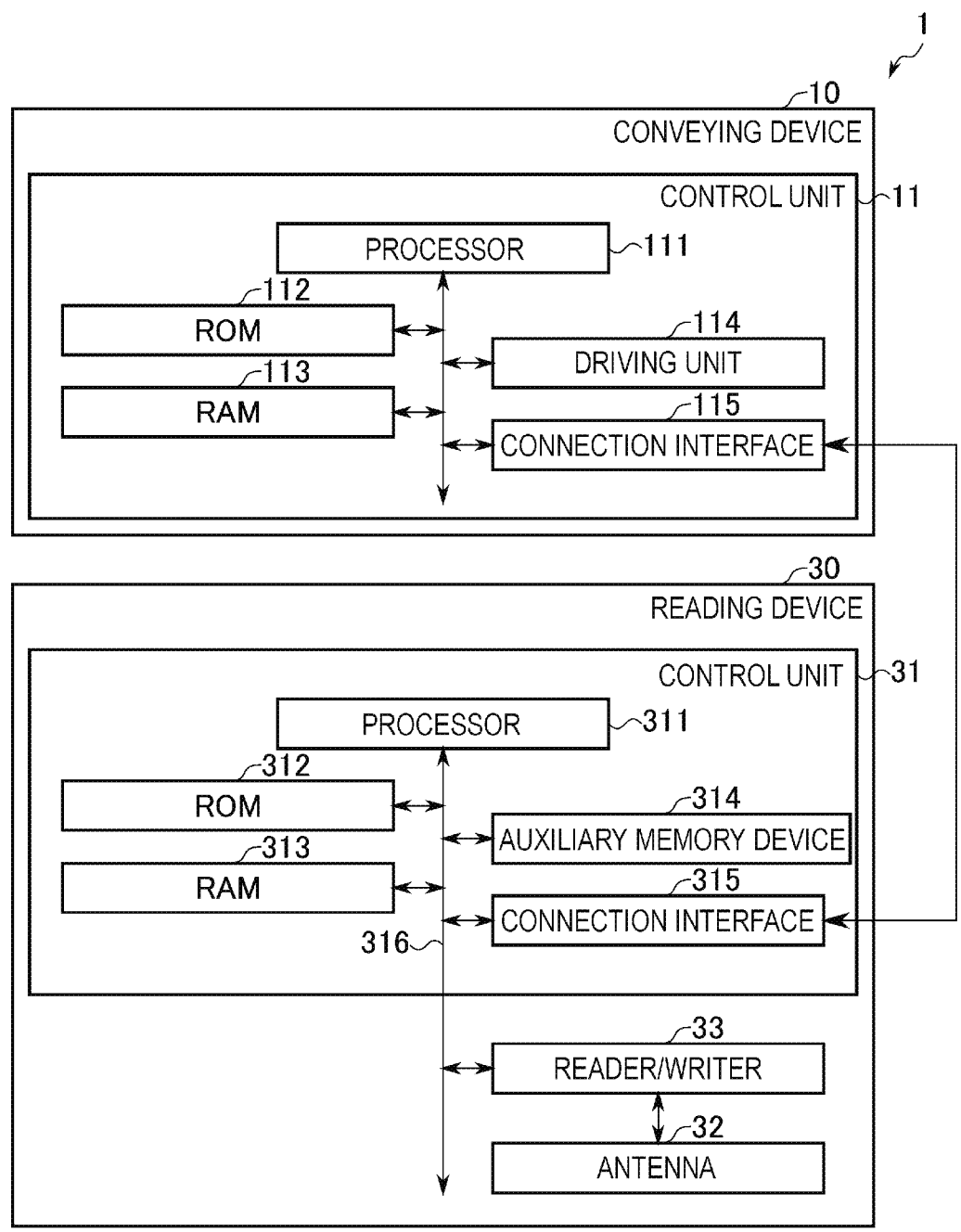
FIG. 3 is a block diagram of components in the specimen inspection system.

FIG. 1 and FIG. 2 illustrate two views of a specifying unit 100 of a specimen inspection system 1 (see FIG. 3). The two views include a top view and a side view. FIG. 1 illustrates a side view of the specifying unit 100 of the specimen inspection system 1. FIG. 2 illustrates a top view of the specifying unit 100 of the specimen inspection system 1. The specimen inspection system 1 performs an inspection of blood placed in a blood collection tube, the blood collection tube and/or the blood in the tube may be referred to as a specimen. Here, the specimen inspection system 1 includes the specifying unit 100. The specifying unit 100 specifies a location in a specimen rack at which the blood collection tube is placed. For example, the specifying unit 100 includes a conveying device 10 (see FIG. 3), a specimen rack 20, a blood collection tube 21, and a reading device 30 (see FIG. 3). The specimen inspection system 1 is an example of a management system or a conveyance system.

The conveying device 10 is a device configured to move the specimen rack 20. For example, the conveying device 10 includes a control unit 11, a conveyance path 12, and a conveyance table 13.

For example, the control unit 11 performs processes such as calculations and controls necessary for the operation of the conveying device 10. Details of the control unit 11 will be described below.

For example, the conveyance path 12 is a rail or a guide for conveying the specimen rack 20. The conveyance path 12 is formed, such that the blood collection tube 21 passes in front of an antenna 16. The conveyance table 13 is a table on which the specimen rack 20 can be placed. The conveyance table 13 moves along the conveyance path 12 while the specimen rack 20 is on the conveyance table 13. For example, the conveying device 10 places the specimen rack 20 on the conveyance table 13. For example, the conveying device 10 pulls out one specimen rack 20 from a specimen tray on which a plurality of specimen racks 20 have been placed, and then places the specimen rack 20 on the conveyance table 13. Alternatively, the specimen rack 20 may be manually placed on the conveyance table 13 by a user.

The specimen rack 20 is configured to accommodate a plurality of blood collection tubes 21 that are standing and lined up. Specifically, the specimen rack 20 includes a row of holes or the like for accommodating the blood collection tubes 21. Although the specimen rack 20 has a linear shape in FIG. 1 and FIG. 2, the specimen rack 20 may also have a circular shape in some examples. The specimen rack 20 may be integrated with the conveyance table 13. The specimen rack 20 is an example of an article holding table configured to hold the blood collection tube 21. Typically, the blood collection tube 21 has a cylindrical shape with a diameter from 12 mm to 16 mm. For example, the blood collection tube 21 is made of a resin. The blood collection tube 21 is attached to a wireless tag 22, which may be an RFID tag incorporated in a label. For example, a label including the wireless tag 22 is attached to the blood collection tube 21. Alternatively, the wireless tag 22 may be embedded in the blood collection tube 21. The method of attaching the wireless tag 22 to the blood collection tube 21 is not limited and other attachment methods may be used.

The wireless tag 22 is typically a passive tag, but may also be a semi-active tag or an active tag. The wireless tag 22 includes a memory and the like for storing information. For example, the memory stores information including a patient identifier (ID). A patient ID is identification information uniquely assigned to each patient. The wireless tag 22 transmits back a radio wave carrying stored information in response to the reception of a radio wave instructing a reading of information from the wireless tag. The wireless tag 22 writes information in the memory in response to the reception of a radio wave instructing a write of information to the wireless tag 22. The frequency of a radio wave used for communication by the wireless tag 22 is, for example, a band around 920 MHz. The information stored in the wireless tag 22 is referred to as wireless tag information.

The reading device 30 reads and writes information from and to the wireless tag 22. For example, the reading device 30 includes a control unit 31, a reader-writer 33, and an antenna 32. The reading device 30 is one example of a management device.

The control unit 31 performs processes such as calculations and controls necessary for the operation of the reading device 30. Details of the control unit 31 will be described below.

The antenna 32 transmits a radio wave to the wireless tag 22. The antenna 32 also receives a radio wave transmitted from the wireless tag 22. The reader-writer 33 demodulates the radio wave transmitted from the wireless tag 22 and received by the antenna 32. As a result, the reader-writer 33 reads information written in the wireless tag 22 in cooperation with the antenna 32. The reader-writer 33 puts information to be transmitted to the wireless tag 22 in a radio wave by modulating the radio wave. The reader-writer 33 writes information to the wireless tag 22 in cooperation with the antenna 32. Accordingly, the reader-writer 33 has a function as a reader for reading information written in the wireless tag 22 and a function as a writer for writing information to the wireless tag 22.

The reader-writer 33 measures and outputs the phase value of a radio wave received from the wireless tag 22. An output phase value is input to the control unit 31. The reader-writer 33 represents, for example, a phase value in the range from 0 degrees to 180 degrees.

FIG. 3 is a block diagram showing an example of the main configuration of components included in the specimen inspection system according to embodiments.

The control unit 11 of the conveying device 10 includes, for example, a processor 111, a read-only memory (ROM) 112, a random-access memory (RAM) 113, a driving unit 114, and a connection interface 115. These components are connected to one another via a bus 116 or the like.

The processor 111 corresponds to a central part of a computer configured to perform processes such as calculations and controls necessary for the operation of the control unit 11. The processor 111 controls each component to realize various functions of the control unit 11 based on a program such as system software, application software, firmware stored in the ROM 112, or the like. Part or all of the programs may be embedded in the circuit of the processor 111. The processor 111 is, for example, a central processing unit (CPU), a micro processing unit (MPU), a system on a chip (SoC), a digital signal processor (DSP), a graphics processing unit (GPU), an application specific integrated circuit (ASIC), a programmable logic device (PLD), or a field-programmable gate array (FPGA). Alternatively, processor 111 is a combination of a plurality of above-stated examples. The processor 111 is an example of a conveyance control unit.

The ROM 112 corresponds to a main storage device of a computer including the processor 111 as the central part. The ROM 112 is non-volatile memory used exclusively for reading data. The ROM 112 stores the above-stated program. The ROM 112 stores data or various parameters used when the processor 111 performs various processes.

The RAM 113 corresponds to a main storage device of a computer including the processor 111 as the central part. The RAM 113 is memory used for reading and writing data. The RAM 113 is used as a so-called work area or the like for temporarily storing data used when the processor 111 performs various processes.

The driving unit 114 is driven to transport the specimen rack 20. The driving unit 114 includes a motor and the like.

The connection interface 115 is an interface for connecting the conveying device 10 to the reading device 30. Communications between the conveying device 10 and the reading device 30 are performed via the connection interface 115.

The bus 116 includes a control bus, an address bus, a data bus, and the like, and transmits signals transmitted and received by the components of the conveying device 10.

For example, the control unit 31 of the reading device 30 includes a processor 311, a ROM 312, a RAM 313, an auxiliary memory device 314, and a connection interface 315. Then, these components are connected to one another via a bus 316 or the like.

The processor 311 corresponds to a central part of a computer configured to perform processes such as calculations and controls necessary for the operation of the control unit 31. The processor 311 controls each component to realize various functions of the control unit 31 based on a program such as system software, application software, firmware stored in the ROM 312, the auxiliary memory device 314, or the like. Part or all of the programs may be embedded in the circuit of the processor 311. The processor 311 is, for example, a CPU, an MPU, an SoC, a DSP, a GPU, an ASIC, a PLD, or an FPGA. Alternatively, processor 311 is a combination of a plurality of above-stated examples. The processor 311 is an example of a processing unit.

The ROM 312 corresponds to a main storage device of a computer including the processor 311 as the central part. The ROM 312 is non-volatile memory used exclusively for reading data. The ROM 312 stores the above-stated program. The ROM 312 stores data or various parameters used when the processor 311 performs various processes.

The RAM 313 corresponds to a main storage device of a computer including the processor 311 as the central part. The RAM 313 is memory used for reading and writing data. The RAM 313 is used as a so-called work area or the like for temporarily storing data used when the processor 311 performs various processes.

The auxiliary memory device 314 corresponds to an auxiliary memory device of a computer including the processor 311 as the central part. The auxiliary memory device 314 is, for example, an electric erasable programmable read-only memory (EEPROM), a hard disk drive (HDD), a solid state drive (SSD), or an embedded MultiMediaCard (eMMC). The auxiliary memory device 314 may store the above-stated program. The auxiliary memory device 314 stores data used when the processor 311 performs various processes, data generated by a process of the processor 311, various parameters, and the like.

The program stored in the ROM 312 or the auxiliary memory device 314 includes a program for executing processes described below. For example, the control unit 31 is provided to an administrator of the control unit 31 or the like in a state in which the program has already been stored in the ROM 312 or the auxiliary memory device 314. However, the control unit 31 may be provided to the administrator or the like without the program already being stored in the ROM 312 or the auxiliary memory device 314. The control unit 31 may be provided to the administrator or the like with a program other than the program being stored in the ROM 312 or the auxiliary memory device 314. Then, a program for executing processes to be described below may be separately provided to the administrator or the like and may be written to the ROM 312 or the auxiliary memory device 314 under the manipulation of the administrator or a service person. The transfer of the program can be realized, for example, by writing the program on a removable storage medium such as a magnetic disk, a magneto-optical disk, an optical disk, or a semiconductor memory or by downloading via a network or the like.

The connection interface 315 is an interface for connecting the conveying device 10 to the reading device 30. Communications between the conveying device 10 and the reading device 30 are performed via the connection interface 315.

The bus 316 includes a control bus, an address bus, a data bus, and the like, and transmits signals transmitted and received by the components of the reading device 30.

Figure 4:
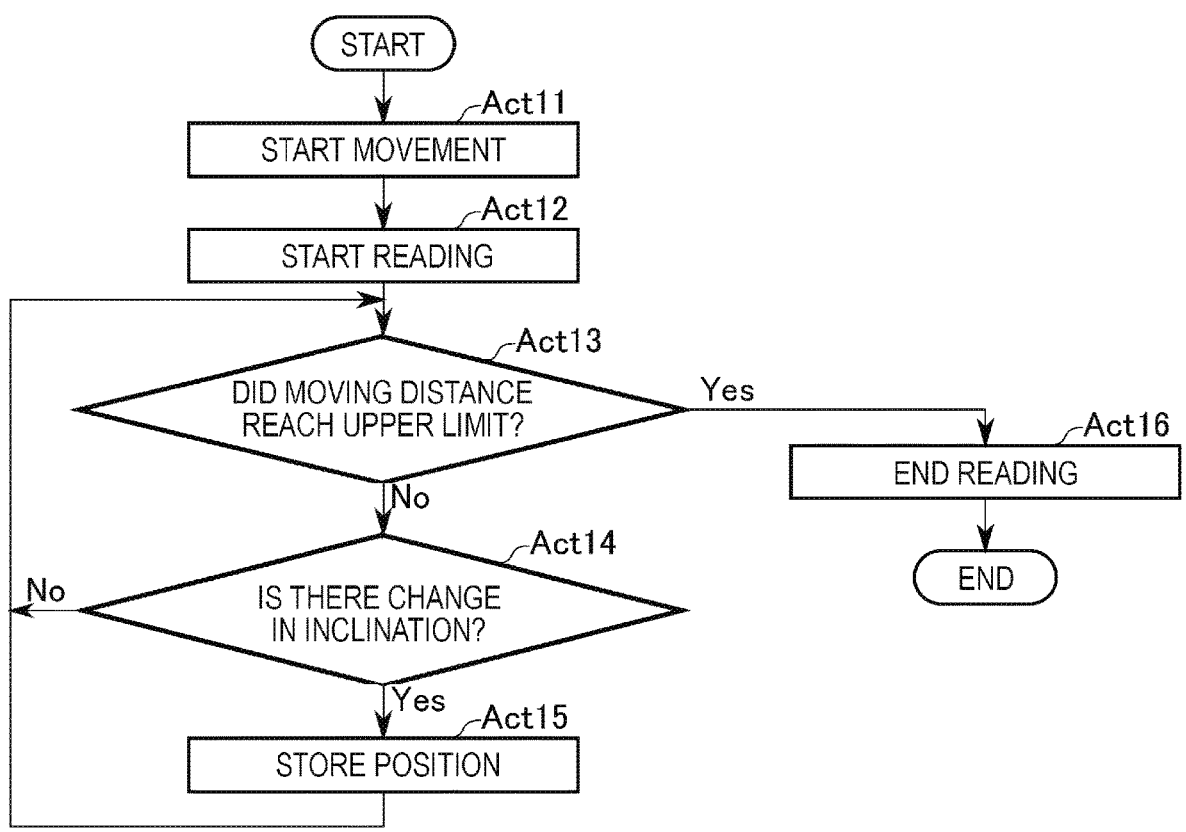
FIG. 4 is a flowchart showing an example of processes according to the first embodiment by a processor of a reading device shown in FIG. 3.

Hereinafter, the operation of the specimen inspection system 1 according to an embodiment will be described with reference to FIG. 4 and the like. The details of processes in the following description of the operation are merely an example, and various processes capable of obtaining equivalent results can be appropriately used. FIG. 4 is a flowchart of a process by the processor 311 of the reading device 30. The processor 311 executes this process based on a program stored in, for example, the ROM 312 or the auxiliary memory device 314.

In Act 11, the processor 311 of the reading device 30 causes the conveyance table 13 to move along the conveyance path 12. That is, the processor 311 instructs the connection interface 315 to transmit a move command to the control unit 11. The move command is a command instructing to start a movement of the conveyance table 13. In response to the instruction, the connection interface 315 transmits a transfer command to the conveying device 10. The transmitted move command is received by the connection interface 115 of the conveying device 10. The move command received by the connection interface 115 is input to, for example, the processor 111. The processor 111 controls the driving unit 114 to start a movement of the conveyance table 13 in response to the input of the move command. The conveyance table 13 starts moving along the conveyance path 12.

In Act 12, the processor 311 starts the operation of the reader-writer 33. That is, the processor 311 controls the reader-writer 33 to be able to read information from the wireless tag 22.

In Act 13, the processor 311 determines whether the moving distance of the conveyance table 13 reached an upper limit. That is, the processor 311 determines whether the moving distance after the conveyance table 13 started to move in Act 11 became equal to or more than a predetermined distance. When the moving distance of the conveyance table 13 did not reach the upper limit, the processor 311 determines No in Act 13 and the process proceeds to Act 14.

In Act 14, the processor 311 determines whether the sign (positive or negative) of the inclination of the phase is changed. The change of the sign (positive or negative) of the inclination of the phase will be described below. The processor 311 determines No in Act 14 and the process returns to Act 13 when the sign (positive or negative) of the inclination of the phase is not changed. Thus, the processor 311 repeats Act 13 and Act 14 until the moving distance of the conveyance table 13 reaches the upper limit or the sign (positive or negative) of the inclination of the phase changes.

Figure 5:
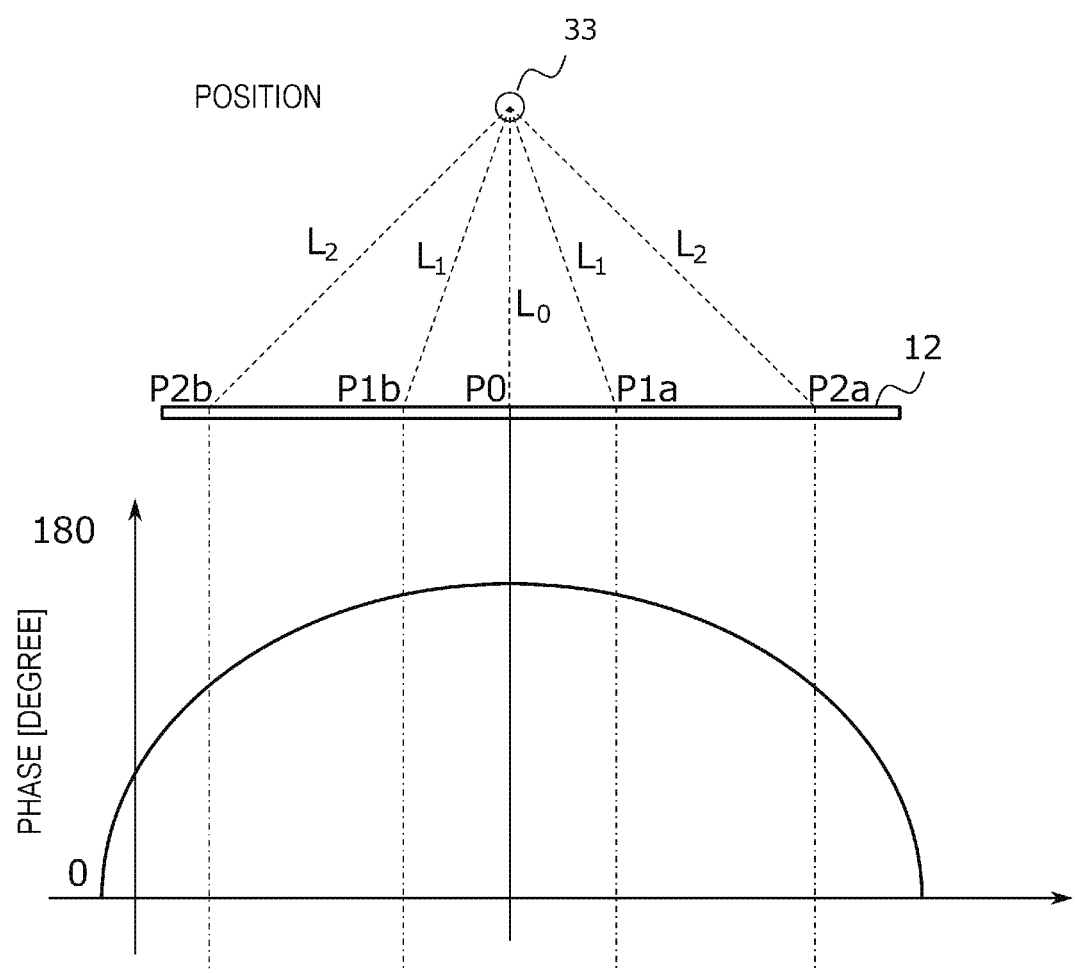
FIG. 5 depicts a change in phase when a wireless tag passes in front of an antenna.
Figure 6:
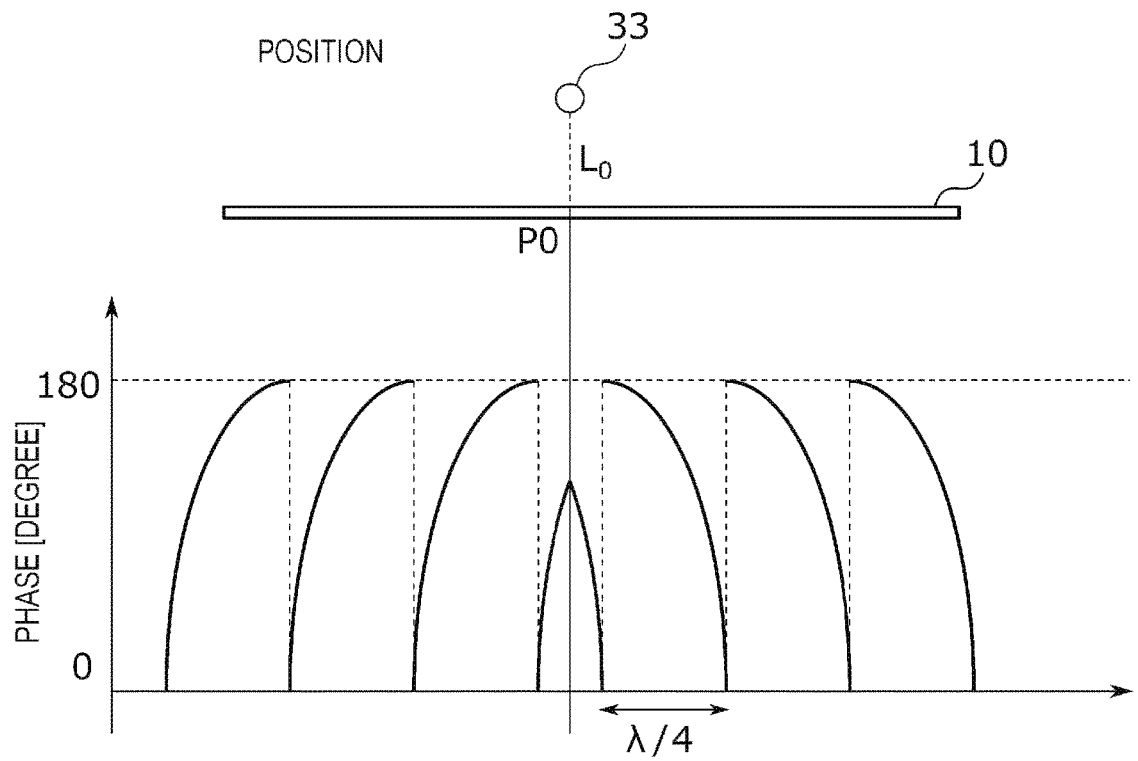
FIG. 6 depicts a change in phase when a wireless tag passes in front of the antenna.
Figure 7:
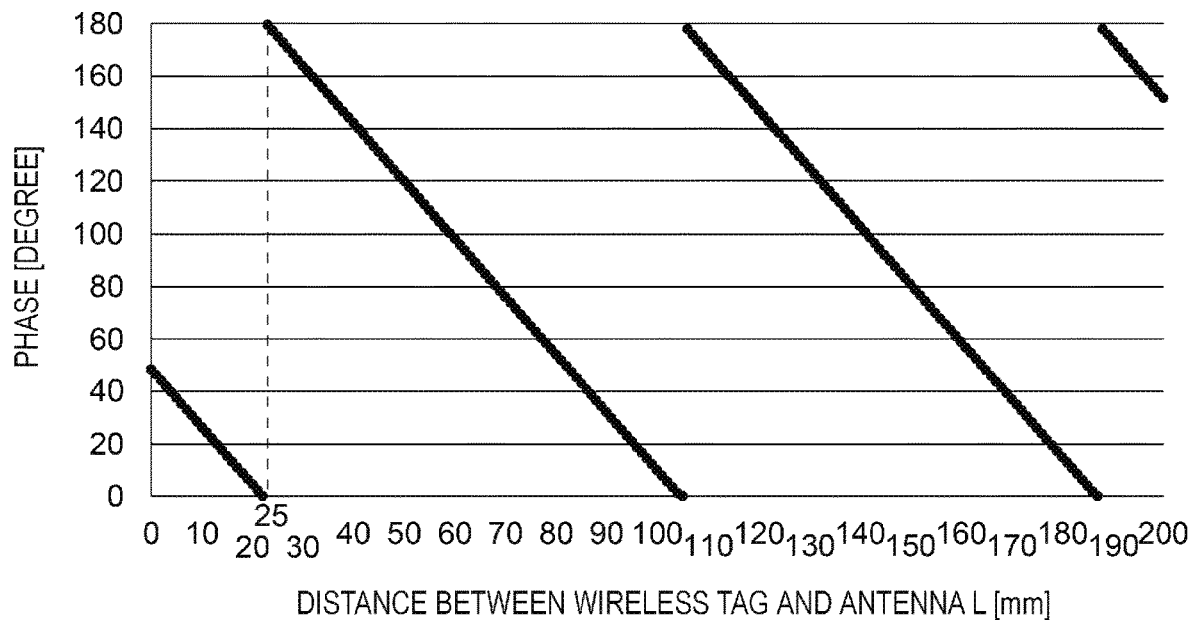
FIG. 7 is a graph depicting a relationship of distances between a wireless tag and an antenna and phases.

The change of phase when the wireless tag 22 passes in front of the antenna 32 is shown in FIGS. 5 and 6. As shown in FIG. 5, when the wireless tag 22 is at a front position P0 of the antenna 32, the distance between the antenna 32 and the wireless tag 22 is the smallest. The distances from the antenna 32 to P1a and P1b are equal to the distances from the antenna 32 to P2a and P2b around P0, respectively. Since phase value is determined by the distance between the antenna 32 and the wireless tag 22, the graph is symmetrical around P0. Therefore, when the wireless tag 22 passes in front of the antenna 32, the sign (positive or negative) of the inclination of the phase value is inverted. By using the same, the processor 311 can detect that the wireless tag 22 passed in front of the antenna 32. The reader-writer 33 represents a phase value in the range from 0 degrees to 180 degrees as described above. Therefore, as shown in FIG. 6, discontinuous points appear at a quarter wavelength period. The relationship of a distance L between the wireless tag 22 and the antenna 32 and phase is as shown in FIG. 7. FIG. 7 shows the relationship of the distance L between the wireless tag 22 and the antenna 32 and phase. By setting L0 to about 25 mm or more, the phase value at the time when the wireless tag 22 passes may be about 180 degrees or less than 180 degrees. As a result, the range of about ¼ wavelength before and after an antenna front surface P0 is a range where there is no phase value discontinuous point. Therefore, by limiting the range in which the antenna 32 reads the wireless tag 22 to a range of about ¼ wavelength before and after the antenna front surface P0, discontinuous points may be eliminated in data processing of phase values. This facilitates detection of the inversion of the inclination of the phase value. For example, the reader-writer 33 is controlled to limit the range at which the wireless tag 22 can be read. The reader-writer 33 may operate to limit a reading range through a hardware configuration or software. When a distance L0 is increased, the variation of a distance to the wireless tag 22 passing in front of the antenna 32 is reduced. For this reason, the variation of phase value is also reduced. Therefore, it is preferable to set the distance L0 to a small value. A reading range limited as described above is an example of a communication area of a range in which no discontinuous point appears in the phase of a radio wave received from the wireless tag 22.

The processor 311 determines Yes in Act 14 and the process proceeds to Act 15 when the sign (positive or negative) of the inclination of the phase is changed in the reception standby state of Act 13 and Act 14. In Act 15, the processor 311 associates the position of the wireless tag 22 (the blood collection tube 21), which caused the determination of Yes in the preceding process of Act 14, with a patient ID stored in the wireless tag 22 and stores a result of the association in the RAM 313 or the like. The wireless tag 22 is the wireless tag 22 that passed right before in front of the antenna 32. The processor 311 stores the position of the wireless tag 22 based on, for example, the moving distance of the conveyance table 13. The processor 311 returns to Act 13 after the process of Act 15.

When the moving distance of the conversation base 13 reached the upper limit while being in the reception standby state of Act 13 and Act 14, the processor 311 determines Yes in Act 13 and the process proceeds to Act 16.

In Act 16, the processor 311 controls the reader-writer 33 to stop the operation of the reader-writer 33. After the process of Act 16, the processor 311 ends the processes shown in FIG. 4. Then, the specimen inspection system inspects each of the specimens in the blood collection tube 21 placed on the specimen rack 20 placed on the conveyance table 13.

As described above, by repeating Act 13 to Act 15 until the moving distance of the conveyance table 13 reaches the upper limit, the processor 311 can remember positions of all of the blood collection tubes 21 placed on the specimen rack 20 placed on the conveyance table 13.

According to the specimen inspection system 1 according to the first embodiment, the reading device 30 specifies the position based on the phase of a radio wave transmitted by the wireless tag 22. Therefore, the reading device 30 is capable of specifying the position at high accuracy.

Second Embodiment

The configuration of a specimen inspection system 1b according to a second embodiment is the same as the configuration of the specimen inspection system 1 according to the first embodiment. However, in the second embodiment, a specimen rack 20b is used instead of the specimen rack 20. Therefore, descriptions are omitted except for the specimen rack 20b.

Figure 8:
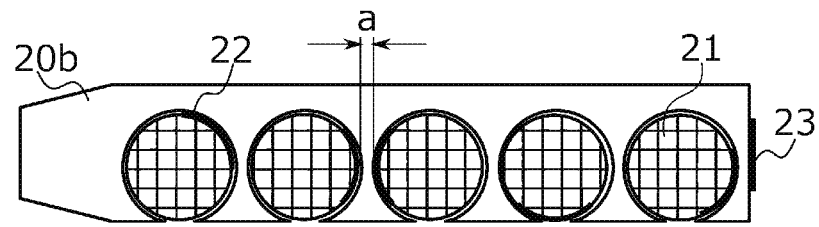
FIG. 8 illustrates a top view of a specimen rack according to a second embodiment.

FIG. 8 illustrates a top view of the specimen rack 20b according to the second embodiment. A wireless tag 23 is attached to the specimen rack 20b. The specimen rack 20b is an example of an article holding table.

A position for attaching the wireless tag 23 is the leading part of the specimen rack 20b in a conveyance direction. The hardware configuration of the wireless tag 23 is similar to that of the wireless tag 22. The wireless tag 23 stores, for example, information that can be used to specify the wireless tag 23 as the wireless tag 23 attached to the specimen rack 20b. A width "a" is, for example, 6 mm. The reader-writer 32 and the antenna 33 communicate with the wireless tag 23 in the same manner as they communicate with the wireless tag 22.

Figure 9:
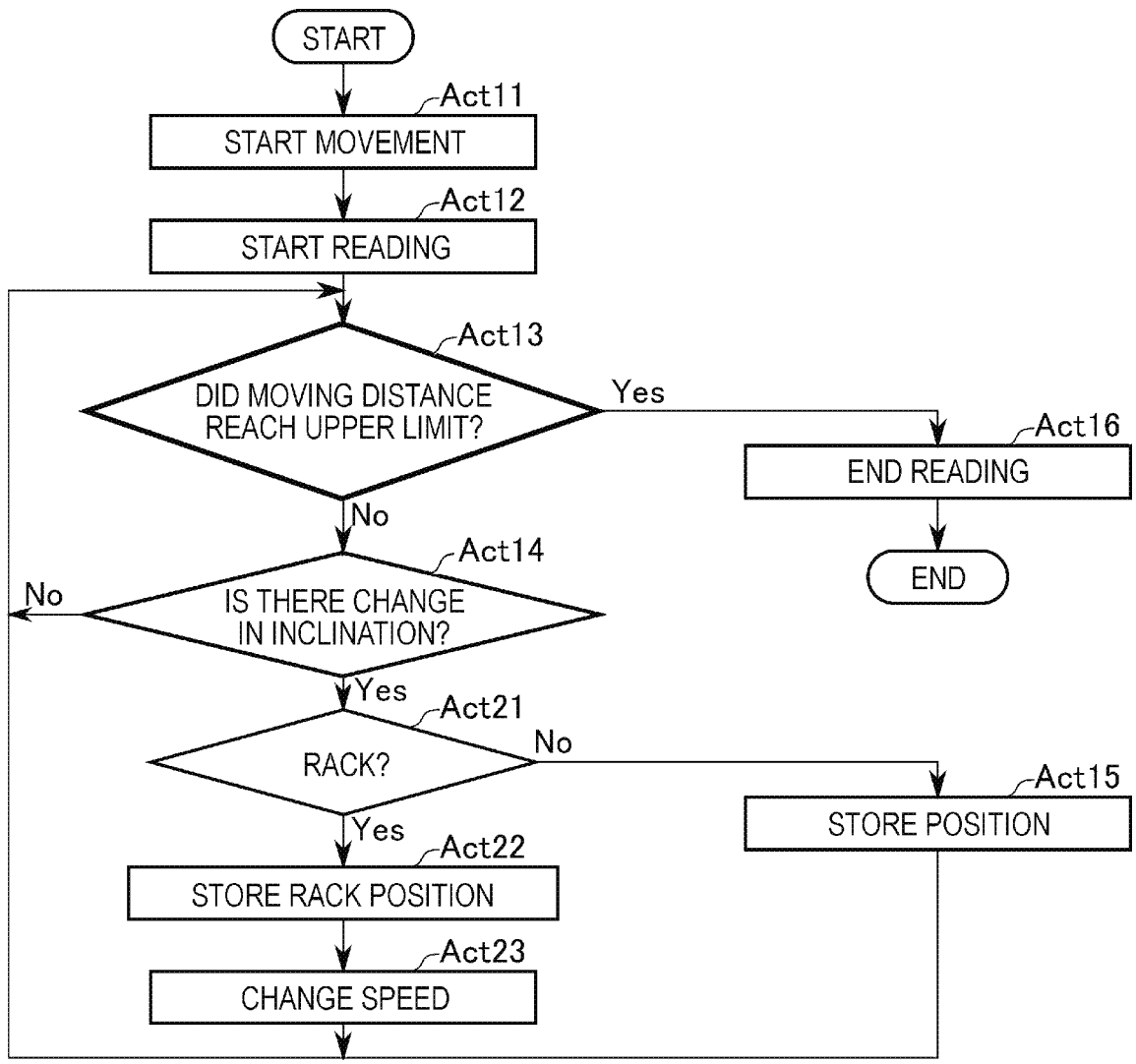
FIG. 9 is a flowchart showing an example of processes according to the second embodiment by the processor of the reading device shown in FIG. 3.

Hereinafter, an operation of the specimen inspection system 1b according to the second embodiment will be described with reference to FIG. 9 and the like. The details of processes in the following description of the operation are merely an example, and various processes capable of obtaining equivalent results can be appropriately used. FIG. 9 is a flowchart of a process by the processor 311 of the reading device 30. The processor 311 executes this process based on a program stored in, for example, the ROM 312 or the auxiliary memory device 314.

In the second embodiment, the processor 311 processes the wireless tag 23 in the same manner as the wireless tag 22 in Act 12 to Act 15.

When the processor 311 determines Yes in Act 14, the process proceeds to Act 21. In Act 21, the processor 311 determines whether a wireless tag read right before is a wireless tag attached to the specimen rack 20. When the read wireless tag is the wireless tag 22, the processor 311 determines No in Act 21 and the process proceeds to Act 15. On the other hand, when the read wireless tag is the wireless tag 23, the processor 311 determines Yes in Act 21 and the process proceeds to Act 22.

In Act 22, the processor 311 stores the position of the specimen rack 20 in the RAM 313 or the like. The processor 311 stores the position of the specimen rack 20 based on, for example, the moving distance of the conveyance table 13.

In Act 23, the processor 311 slows down the moving speed of the conveyance table 13. That is, the processor 311 instructs the connection interface 315 to transmit a low-speed command to the control unit 11. The low-speed command is a command instructing to reduce the moving speed of the conveyance table 13. In response to the instruction, the connection interface 315 transmits a low-speed command to the conveying device 10. The transmitted low-speed command is received by the connection interface 115 of the conveying device 10. After the process of Act 23, the process returns to Act 13. The low-speed command received by the connection interface 115 is input to, for example, the processor 111. The processor 111 controls the driving unit 114 to reduce the moving speed of the conveyance base 13 in response to the input of the low-speed command.

The specimen inspection system 1b according to the second embodiment can obtain the same effect as the specimen inspection system 1 according to the first embodiment. The specimen inspection system 1b according to the second embodiment reduces the moving speed of the conveyance table 13 in response to the wireless tag 23 attached to the specimen rack 20 passing in front of the antenna 32. Therefore, the specimen inspection system 1b can improve accuracy of specifying the position of the blood collection tube 21.

The above embodiments can be modified as follows. In the first embodiment and the second embodiment, the wireless tag 22 passes in front of the antenna 32 as the specimen rack 20 moves. Alternatively, the antenna rack 20 may be stationary and the antenna 32 may move.

The reader-writer may represent a phase value in a range other than the range from 0 degrees to 180 degrees. For example, the reader-writer may represent a phase value in a range from 0 degrees to 360 degrees.

In the first embodiment and the second embodiment, the case of specifying the position of a blood collection tube 21 is described using a specimen inspection system 1 as an example. However, in other examples, identification targets are not limited to a blood collection tube 21. For example, an embodiment may be a device used for managing or sorting any physical distribution of items including wireless tags or the like. The device can specify a position of an item or article being conveyed in the same manner as described in the above example embodiments for a blood collection tube 21. Such an item/article may be placed on a dedicated table and conveyed. The dedicated table in this context may be referred to as an article holding table.

The processor 111 and the processor 311 may realize some or all of the processes realized by software in the above example embodiments through use of dedicated or specialized hardware and/or a circuit configuration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A management device, comprising:
    an antenna positionable at a position near a conveyance path;
    a reader configured to output wireless tag information based on a radio wave received by the antenna; and
    a processor configured to:
        detect sign change of a slope of a phase of the radio wave received by the antenna, the sign change including change of the slope of the phase of the radio wave from a minus value to a plus value or from a plus value to a minus value,
        detect passage of an article through a predetermined position on the conveyance path based on an identifier of the article included in the wireless tag information and the detected sign change in the slope of the phase of the radio wave received by the antenna, the article including a wireless tag that outputs the radio wave,
        determine a position of the article based on a conveyed distance of the article since the detected sign change in the slope of the phase of the radio wave received by the antenna,
        store the position of the article in correspondence with the identifier of the article, and
        cause a conveyance speed of articles along the conveyance path to be decreased if the article identified by the identifier is a predetermined article.

2. The management device according to claim 1, further comprising:
    a conveyer along the conveyance path; and
    a conveyer driver configured to drive the conveyer, wherein
    the processor is configured to cause a command to be transmitted to the conveyer driver to cause the conveyance speed to be decreased.

3. The management device according to claim 2, wherein the processor is configured to:
    cause the conveyance speed of the conveyer to be decreased when the article identified by the identifier is a first predetermined article, and
    cause the conveyance speed of the conveyer to be maintained when the article identified by the identifier is a second predetermined article.

4. The management device according to claim 3, wherein the first predetermined article is a sample tube container, and the second predetermined article is a sample tube.

5. The management device according to claim 1, wherein the antenna is configured to have a maximum communication range in which there is no discontinuity in phase of the radio wave.

6. The management device according to claim 1, wherein the processor is further configured to:
    determine a conveyed distance along the conveyance path, and
    disable the reader upon determining that the conveyed distance has reached a predetermined threshold.

7. The management device according to claim 1, wherein the wireless tag is a radio frequency identifier (RFID) tag.

8. An operating method of a management device including an antenna positioned near a conveyance path and a reader configured to output wireless tag information based on a radio wave received by the antenna, the method comprising:
    detecting sign change of a slope of a phase of the radio wave received by the antenna, the sign change including change of the slope of the phase of the radio wave from a minus value to a plus value or from a plus value to a minus value;
    detecting passage of an article through a predetermined position on the conveyance path based on an identifier of the article included in the wireless tag information and the detected sign change in the slope of the phase of the radio wave, the article including a wireless tag that outputs the radio wave;
    determining a position of the article based on a conveyed distance of the article since the detected sign change in the slope of the phase of the radio wave received by the antenna;
    storing the position of the article in correspondence with the identifier of the article; and
    decreasing a conveyance speed of articles along the conveyance path if the article identified by the identifier is a predetermined article.

9. The operating method according to claim 8, wherein the management device further includes a conveyer along the conveyance path and a conveyer driver configured to drive the conveyer, the method further comprising:
    transmitting a command to the conveyer driver to cause the conveyance speed to be decreased.

10. The operating method according to claim 9, further comprising:
    decreasing the conveyance speed of the conveyer when the article identified by the identifier is a first predetermined article, and
    maintaining the conveyance speed of the conveyor when the article identified by the identifier is a second predetermined article.

11. The operating method according to claim 10, wherein the first predetermined article is a sample tube container, and the second predetermined article is a sample tube.

12. The operating method according to claim 8, wherein the antenna is configured to have a maximum communication range in which there is no discontinuity in the phase of the radio wave.

13. The operating method according to claim 8, further comprising:

determining a conveyed distance along the conveyance path, and disabling the reader upon determining that the conveyed distance has reached a predetermined threshold.

14. The operating method according to claim 8, wherein the wireless tag is a radio frequency identifier (RFID) tag.

* * * * *